United States Patent [19]

Ostgaard et al.

[11] Patent Number: 5,602,037

[45] Date of Patent: Feb. 11, 1997

[54] COMBINATION REAGENT HOLDING AND TEST DEVICE

[75] Inventors: Roy Ostgaard, Plantation, Fla.; Stephen Schoenberg, Redwood City; Thomas R. Stone, San Francisco, both of Calif.; Sourav K. Kundu, Cooper City, Fla.; Ted S. Geiselman, Bolton, Mass.

[73] Assignee: Dade International, Inc., Deerfield, Ill.

[21] Appl. No.: 269,184

[22] Filed: Jun. 30, 1994

[51] Int. Cl.$^6$ .................................................. G01N 33/86
[52] U.S. Cl. .................. 436/69; 436/70; 422/58; 422/61; 422/73; 422/82.05; 422/101; 422/102
[58] Field of Search .................... 436/69, 70; 422/58, 422/61, 73, 82.05, 101, 102

[56] References Cited

U.S. PATENT DOCUMENTS

| | | | |
|---|---|---|---|
| 2,616,796 | 11/1952 | Schilling et al. | 436/69 |
| 3,219,421 | 11/1965 | Schwarz et al. | 436/69 |
| 3,267,362 | 8/1966 | Page | 324/30 |
| 3,267,364 | 8/1966 | Page et al. | 324/30 |
| 3,268,804 | 8/1966 | Young | 436/69 |
| 3,539,300 | 11/1970 | Stone | 422/73 |
| 3,605,010 | 9/1971 | Folus | 324/30 R |
| 3,694,161 | 9/1972 | Kleszynski et al. | 23/230 B |
| 3,914,985 | 10/1975 | von Behrens | 73/61.4 |
| 3,918,908 | 11/1975 | Moyer et al. | 23/230 B |
| 4,533,519 | 8/1985 | Baugh et al. | 422/73 |
| 4,534,939 | 8/1985 | Smith | 422/61 |
| 4,599,219 | 7/1986 | Cooper et al. | 422/61 |
| 4,604,804 | 8/1986 | Sparks | 30/294 |
| 4,604,894 | 8/1986 | Kratzer et al. | 73/64.1 |
| 4,752,449 | 6/1988 | Jackson et al. | 422/73 |
| 4,777,141 | 10/1988 | Calzi et al. | 436/69 |
| 4,780,417 | 10/1988 | Kim | 436/20 |
| 4,780,418 | 10/1988 | Kratzer | 436/69 |

(List continued on next page.)

FOREIGN PATENT DOCUMENTS 0515883 12/1992 European Pat. Off. .
2096329 9/1985 United Kingdom .

OTHER PUBLICATIONS

G. Dietrich et al., *Infusionstherapie*, 17:214–216 (1990), "Primary Hemostatis in Hemodilution—2) Infusion Solutions".

G. Dietrich et al., *Lab. Med.*, 17:317, (1993), "The In Vitro Bleeding Test Standardization Of The Methodical Procedure".

(List continued on next page.)

*Primary Examiner*—Jill Warden
*Assistant Examiner*—Sharidan Carrillo
*Attorney, Agent, or Firm*—Linda M. Buckley; Cara Z. Lowen

[57] ABSTRACT

The present invention provides novel test cartridges for use in the assay of liquid samples and methods of carrying out such assays. These test cartridges are particularly useful in assays which include at least one step during which the sample to be assayed and one or more components of the assay system are kept separated by a pierceable member. The test cartridges comprise a housing through which the sample flows during the assay. The housing includes a holding chamber for holding the sample and a test chamber separated by a pierceable member. The test chamber further includes a partition member which has an opening therethrough and includes at least one reagent for the assay. A transfer member movably mounted in the test chamber can move towards and pierce the pierceable member and contact the liquid sample in the holding chamber. When the transfer member has been moved towards and pierces the pierceable member to contact the liquid sample and a negative pressure is created in the test chamber, liquid sample moves through the transfer member, into the test chamber and through the opening in the partition member.

24 Claims, 6 Drawing Sheets

U.S. PATENT DOCUMENTS

| | | | |
|---|---|---|---|
| 4,784,944 | 11/1988 | Kolde | 435/13 |
| 4,788,139 | 11/1988 | Ryan | 435/13 |
| 4,812,293 | 3/1989 | McLaurin et al. | 422/69 |
| 4,865,813 | 9/1989 | Leon | 422/101 |
| 5,047,211 | 9/1991 | Sloane, Jr. et al. | 422/73 |
| 5,051,239 | 9/1991 | von der Goltz | 422/73 |
| 5,059,239 | 10/1991 | Seiler | 71/94 |
| 5,089,422 | 2/1992 | Brubaker | 436/69 |
| 5,174,961 | 12/1992 | Smith | 422/73 |
| 5,197,017 | 3/1993 | Carroll et al. | 364/497 |
| 5,223,227 | 6/1993 | Zuckerman | 422/102 |
| 5,246,666 | 9/1993 | Vogler et al. | 422/73 |
| 5,275,953 | 1/1994 | Bull | 436/69 |
| 5,281,661 | 1/1994 | Linnau et al. | 525/54.1 |
| 5,314,826 | 5/1994 | Baugh | 436/69 |
| 5,316,730 | 5/1994 | Blake et al. | 422/73 |
| 5,339,830 | 9/1994 | Blake, III | 128/771 |
| 5,352,413 | 10/1994 | Kratzer | 422/100 |

OTHER PUBLICATIONS

M. A. A. Kratzer et al., *Haemostasis*, 15:363–370 (1985), "Detection of Abnormal Platelet Functions With an In Vitro Model of Primary Haemostasis".

M. A. A. Kratzer et al., *Haemostasis*, 15:357–362 (1985), "Simulation of Primary Haemostasis In Vitro".

V. Kretschmer et al., *Transfus. Sci.*, 14:27–34 (1993), "Determination of Bleeding Risk in Thrombocytopenic Patients Receiving Platelet Substitution".

V. Kretschmer et al., *Blut*, 59:188 (1989), "In Vitro Bleeding Test—A Sensitive Method For The Detection Of Platelet Function Impairment And A Potential Test For The Control Of Low–Dose Aspirin Efficacy".

V. Kretschmer et al., *Thrombosis Research*, 56:593–602 (1989), "In Vitro Bleeding Test—A Simple Method For The Detection Of Aspirin Effects On Platelet Function".

K. J. Ericsson et al., *Eur. J. Haematol.*, 51:152–155 (1993), "Functional Capacity Of Transfused Platelets Estimated By The Thrombostat 4000/2".

dN. Maurin, *The International Journal Of Artificial Organs*, vol. 11, No. 4, (1988), "The in vitro Bleeding Time While Using A Stable Prostacyclin Analogue During Hemodialysis".

T. Tsujinara et al., *Japanese Journal Of Surgery*, vol. 18, No. 1, pp. 430–437, (1988), "Clinical Application Of A New in vitro Bleeding Time Device On Surgical Patients".

R. Alshameeri et al., *Thromb. Haemost* 1993, 69:1146, "Evaluation Of An In Vitro Bleeding Time Device, Thrombostat 4000".

"Platelet Function Analyzer PFA–100", Baxter.

COMBINATION REAGENT HOLDING AND TEST DEVICE

BACKGROUND OF THE INVENTION

In the assay of a sample for the presence or absence of a certain condition or a particular analyte, reagents/components of the assay system are often added at different stages in the assay, i.e., they are not combined until the appropriate stage in the assay. The particular order in which reagents are combined is determined by the requirements of the particular assay. For example, in some systems it is necessary to incubate to bring the sample and/or reagents to a desired temperature before initiating the assay; in two step assays wherein one reaction must precede the other, if reagents for the second reaction interfere with the first reaction then these reagents must not be added until after the first reaction is complete; and so on.

Assays wherein components/reagents are added or combined at various times during the course of the assay are subject to user error and are often cumbersome and inefficient to run. One assay developed to measure the condition of the blood of a patient is a case in point as will be discussed hereinafter.

Hemostasis or stoppage of bleeding involves the interplay of two biochemical pathways which are controlled by various protein factors and formed elements, e.g., platelets. The processes by which blood coagulates as it is presently understood involve a multi-step cascade of activations of the protein factors that culminate in fibrin formation. Various tests have been developed to test the individual steps of this cascade in order to determine whether the blood of a patient can properly clot or whether there is clotting disorder in which there is a deficiency of one or more of the factors necessary for proper clotting. It is well known that the condition of the platelets or the platelet function of blood is one indication of the ability of blood to properly clot.

The primary existing test in use for testing platelet function or Primary Hemostasis on whole human blood is known as the bleeding time test. The bleeding time test which has existed for several decades involves an incision on the forearm of the patient. Accordingly, a test which does not involve an incision and which is also more accurate was developed.

U.S. Pat. Nos. 4,604,894; 4,780,418; and 5,051,239 disclose an assay system which can be used to perform an in vitro test on blood that can be accurately and reproducibly correlated to the in vivo bleeding time test described above, thereby eliminating involvement of the patient. The Thrombostat™ 4000 (Baxter Diagnostics), in current use, is one such system. Platelet function is evaluated in these systems by aspirating anticoagulated whole blood samples at a constant negative pressure through a small aperture positioned at the center of a separating wall which may be non-porous or porous. In systems wherein the separating wall is porous, it is wetted prior to the start of the assay with an activator that activates coagulation of blood platelets. A platelet plug forms at the aperture and the time required for the cessation of blood flow to occur is determined. This time is then correlated to platelet function, i.e., in vivo bleeding time.

The Thrombostat™ 4000 system is not in widespread use, due largely to the present configuration which is costly and does not lend itself to automation for a number of reasons, including limitations of the device which holds the sample to be tested. The device currently used with the Thrombostat™ 4000 consists of three separate parts: a reagent/test chamber, a capillary, and a sample cup. A porous separating wall containing collagen is disposed in the reagent/test chamber. The reagent/test chamber then must be stored in a separate hermetic package apart from the capillary and sample cup to maintain stability of the collagen for the specified shelf life. The capillary and reagent/test chamber must be manually assembled by the operator at the start of each test being performed. Furthermore, the sample to be tested must be pipetted into the sample cup and incubated before the sample cup can be assembled to the capillary and reagent/test chamber. In addition, the incubation step is manually timed by the operator. The separate incubation step requires additional handling after the incubation period, when the operator manually places the assembled capillary and reagent/test chamber into the sample cup and initiates the testing sequence. At the end of the test, the capillary is removed and cleaned for reuse because of its high cost.

It can be seen that the Thrombostat™ 4000 system could be improved by use of a device which eliminates the need for user interaction during a test cycle, which does not require complicated sample handling mechanisms, which eliminates the need for a separate external hermetic package for the reagent/test chambers during shipping and storage and which is disposable. A device which accomplishes these objectives would be generally useful in assay systems wherein certain components/reagents are kept separated or not combined until the appropriate time. Accordingly, such devices are being sought.

SUMMARY OF THE INVENTION

Figure 1:
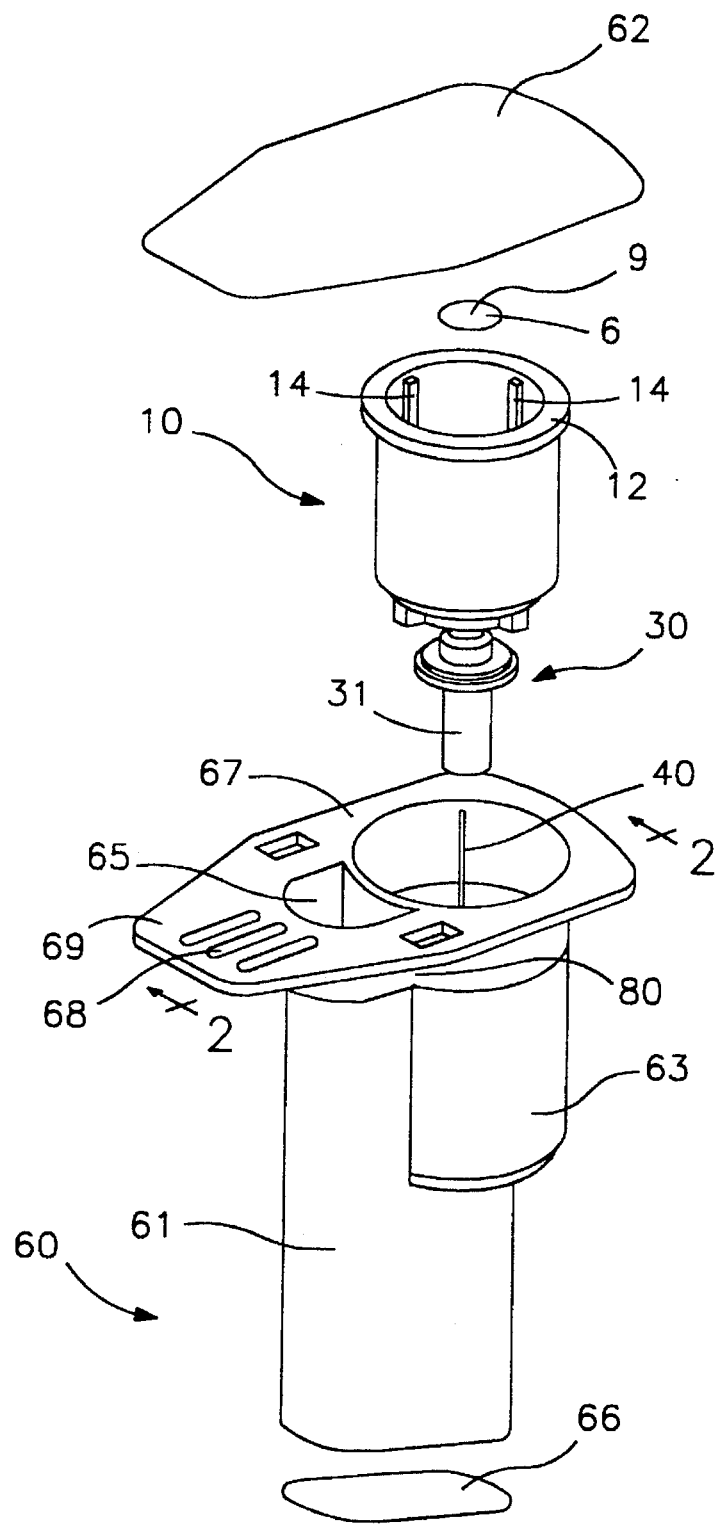
FIG. 1 is an exploded isometric view of components of one preferred device in accordance with the present invention.

The present invention provides test cartridges for use in the assay of a liquid sample, wherein the assay includes at least one step during which the sample to be assayed and one or more components of the assay system are kept separated. In one preferred embodiment of the present invention, the test cartridges are disposable liquid sampling and containing devices particularly useful in automated analysis, wherein the liquid to be assayed flows through the device. The test cartridges of the present invention are especially suited for use in assays which involve the testing of a bodily liquid, such as blood, blood plasma or serum.

In one preferred embodiment of the present invention is provided a test cartridge for use in an assay system for the assay of a liquid sample, the test cartridge comprising a housing through which the sample flows during the assay, the housing comprising:

(a) a holding chamber for holding the liquid sample and a test chamber for receiving the liquid sample from the holding chamber, wherein the holding chamber and test chamber are separated by a pierceable member;

(b) a partition member disposed in the test chamber, the member having an opening therethrough and comprising at least one reagent for the assay; and (c) a transfer member movably disposed in the test chamber so that it can be moved towards and pierce the pierceable member and contact a liquid sample within the holding chamber;

whereby when the transfer member has been moved towards and pierces the pierceable member to contact a liquid sample and a negative pressure is created in the test chamber, liquid sample moves through the transfer member, into the test chamber and through the opening in the partition member.

One preferred test cartridge of the present invention is adapted for use in an assay system which involves an incubation step wherein the sample to be analyzed and other components of the assay are kept separated. This device is particularly suited for assay systems wherein the incubation and testing steps are automatically carried out by an instrument and the incubation step includes heating the sample to be assayed and other components of the assay system to a predetermined temperature at which the assay will be carried out. Such test cartridges are particularly suited for use in assay systems for testing a hemostasis or coagulation function of blood.

One such preferred test cartridge of the present invention is specifically adapted for use in an assay for testing a coagulation function of blood such as the measurement of platelet function, including but not limited to automated versions of those assays described in U.S. Pat. Nos. 4,604,894, 4,780,418, and 5,051,239 discussed above.

In one such preferred embodiment, the test cartridge comprises a housing, wherein the housing comprises:

(a) a holding chamber for receiving a sample of the blood to be tested and a test chamber, wherein the holding chamber and test chamber are separated by a pierceable member;

(b) a partition member disposed in the test chamber, the partition member having an opening therethrough and comprising at least one reagent which activates at least one pathway of the coagulation of blood;

(c) a transfer member movably mounted in the test chamber so that it can be moved towards and pierce the pierceable member; and (d) a receiving chamber disposed in the test chamber between the partition member and the transfer member for receiving blood from the transfer member.

In use, blood is disposed by a user in the holding chamber and the test cartridge is placed in an instrument for incubation. After incubation, the transfer member is moved towards and pierces the pierceable member to contact the blood and a negative pressure is created in the test chamber, blood moves through the transfer member into the receiving chamber and through the opening in the partition member.

The test cartridges of the present invention are intended for use with an instrument which automates some or all of the steps of the assay being conducted. The configuration of the instrument is not particularly important but the test cartridge and instrument must be compatible to accomplish the desired objectives, one of which is the creation of a negative pressure in the test cartridge or a portion thereof so that a liquid sample and/or other reagents can be aspirated through the transfer member as desired.

The design and geometry of the housing and its components is selected based on the assay to be performed. The housing is configured so that the transfer member makes contact with the liquid sample and/or reagents so that a volume of liquid sufficient to carryout the assay can be transferred to the test chamber. When the assay involves an incubation step, a section of the holding chamber contacts heating or cooling elements in the instrument. This section preferably comprises a material which is capable of enhancing the heat transfer.

In one preferred embodiment, the holding chamber is L-shaped, the bottom of the L forming the bottom of the holding chamber and being angled downwardly so that liquid sample placed in the holding chamber will flow easily to the bottom. This configuration also creates additional surface area for contact with heating or cooling elements.

In one preferred embodiment, the test chamber is adapted to receive a sample cup, the sample cup having disposed therein the partition member, the receiving chamber and the transfer member. In such embodiments, the assay takes place in the vicinity of the partition member, the liquid sample being aspirated from the holding chamber through the transfer member into the receiving chamber positioned just below the partition member, and through the opening in the partition member.

The partition member may be porous and wetted with reagents or it may be in the form of a non-porous plate.

In embodiments adapted for testing a coagulation function of blood, the partition member preferably comprises a porous member which is provided with one or more agents capable of initiating the coagulation process in anticoagulated whole blood and blood plasma or initiating platelet aggregation in anticoagulated whole blood and platelet rich plasma. For example, in one preferred device specifically adapted for testing platelet function, the blood entry side of the partition member comprises a collagen material as disclosed in U.S. Pat. Nos. 4,604,894 and 5,051,239 which acts as an activator for platelet function. Also as disclosed, other activators, such as ADP, can if desired also be provided to the porous member. When platelets in the aspirated and anticoagulated blood come in contact with collagen on the porous member, activation and aggregation events take place around the aperture, ultimately forming a platelet plug which occludes the aperture and causes cessation of blood flow.

It has unexpectedly been discovered that these agents can be incorporated into these porous partition members, dried and then reconstituted at the time of the assay.

In preferred test cartridges, the transfer member is a capillary tube. The flow rate of liquid sample through the device can be controlled by varying the length and diameter of the capillary and the dimensions of the capillary tube are selected in order to achieve a flow rate of liquid sample through the test cartridge optimized for the particular test being conducted.

In the case of test cartridges designed for testing platelet function, the rate of flow is such that an appropriate platelet plug can be formed at the opening in the partition member. If the flow rate is too high, a proper plug of clotted blood will not be formed and erroneous test results could be obtained, in addition to excessive sample volume being required.

In embodiments including a sample cup, the test chamber is provided with a two position support for the sample cup to isolate the holding chamber containing the sample during incubation. During the incubation step the sample cup is in a first position which prevents contact of the transfer member with the sample. After the incubation step, the sample cup is moved into the second position, thereby causing the transfer member disposed therein to move towards and pierce the pierceable membrane, and to contact the liquid sample in the holding chamber.

In another preferred test cartridge of the present invention, the housing is provided with a test type identifier that can be read by the instrument which automatically conducts the assay to set up proper test parameters for conducting the desired assay and also to appropriately label the results of the assay as output by the instrument.

In yet another preferred embodiment, the present invention also provides a cassette which is capable of receiving one or more test cartridges of the present invention and maintaining the device in the appropriate position for introduction of the sample to the holding chamber and subsequent transfer to the instrument which automatically carries out the incubation and testing steps.

The test cartridges of the present invention provide a number of significant improvements in carrying out assays wherein reagents/components are added or combined at various times during the course of the assay. In assays involving an incubation step, the sample to be tested is incubated in the same test cartridge in which the assay takes place, thereby reducing user handling and the potential for error. Efficient thermal transfer to minimize incubation time is accomplished by making the bottom surface of the sample holding chamber from a thin, highly thermal conductive material. The transfer member is introduced to the test chamber without need for operator interaction. The housing can be hermetically sealed, if desired, to provide a controlled, low humidity environment for storage. In embodiments including a test type identifier, the identifier can be read by the instrument to set up proper test parameters and to label results output, all without user intervention, thereby eliminating another potential source for error. The cassette to hold the device during addition of the sample to be tested, allows easy handling and loading and unloading from the instrument in which the assay is carried out.

Test cartridges of the present invention adapted for testing platelet function in those assays disclosed in U.S. Pat. Nos. 4,604,894, 4,780,418, and 5,051,239 provide the improvements discussed above. For example, the sample to be tested is incubated in the same device in which the assay takes place, the sample being isolated from the transfer member during this period to eliminate risk of platelet activation and subsequent blockage of the capillary. Moreover, reduced handling by the user reduces the risk of user contamination by the blood.

The test cartridges of the present invention are generally useful in testing blood coagulation and specifically as blood coagulation is affected by various agents which may be present in a patient's blood or by factors which are lacking or impaired and so forth. The test cartridges adapted for use in the platelet function test are useful, for example, presurgically to predict risk of bleeding, in blood banks for donor screening for functional platelets and quality control tests for platelet function prior to administration, and in hospitals in post administration testing to determine how a patient is responding to platelet infusion, and so forth.

The test cartridges of the present invention have been illustrated with one such cartridge specifically adapted for use in an assay for testing platelet functions. However, it can be seen that test cartridges of the present invention can be adapted for other assays which require that components be kept separated until a specific time in the assay and the components can be combined via a transfer member under a negative pressure.

For example, the test cartridges can be adapted for use in assays to quantitate various cell-ligand interactions and binding. In such test cartridges, the ligand is bound to the partition member around the aperture. A cell suspension is then aspirated through the transfer member into the cup and allowed to flow through the aperture. The binding of cells to the ligand present around the aperture partially occludes the aperture and results in a measurable change in the flow rate through the aperture. Measurement of leukocyte interactions to ligands is a good example of one such potential application. The leukocytes are also known to interact with each other and form aggregates which could also be evaluated with the test cartridges of the present invention. The test cartridge could also be adapted for use in assays to investigate cell-cell interactions under shear conditions. One such application is in evaluation of platelet interaction to endothelial cells, where the endothelial cells line the area surrounding the aperture and the platelet suspension is allowed to flow through the aperture under specific shear conditions.

In many enzyme immunoassays, the antigen (or the antibody) is bound to a solid support. When the antibody (or the antigen) is added, an antigen-antibody complex is formed. The amount of this complex is then measured by addition of a substrate which results in formation of color. The individual components of the assay system must be kept separate until the reactions are ready to proceed. The test cartridge described herein could be adapted for the enzyme immunoassay application. In one such test cartridge, the antigen (or the antibody) is bound to the partition member either by absorption or by crosslinkage chemistry. The antibody (or the antigen) is placed in the test chamber at the onset of the test. The antibody solution is aspirated through the transfer member and allowed to react to the antigen present on the membrane. After incubation for a specific period of time, the transfer member is pushed down to the lower chamber piercing the pierceable member separating the two chambers, and the substrate is aspirated through the transfer member into the cup where it reacts to the antigen-antibody complex on the membrane.

It can be seen that the test cartridges of the present invention can be used for a variety of assays.

DETAILED DESCRIPTION OF THE INVENTION

The test cartridges of the present invention will be illustrated with an embodiment specifically adapted for use in an instrument which is capable of carrying out an automated version of those assays for testing platelet function disclosed in U.S. Pat. Nos. 4,604,804, 4,780,418, and 5,051,239. These assays involve an incubation step in the instrument during which the liquid sample of blood to be analyzed and components of the assay are heated to a particular temperature and during this incubation step the sample and assay components are kept separated.

After the incubation step, the instrument causes the transfer member to pierce the pierceable section between the holding and test chambers and to move into contact with the blood, and causes blood to be aspirated through the transfer member by creating a negative pressure in the housing as will be more fully discussed hereinafter.

Figure 2:
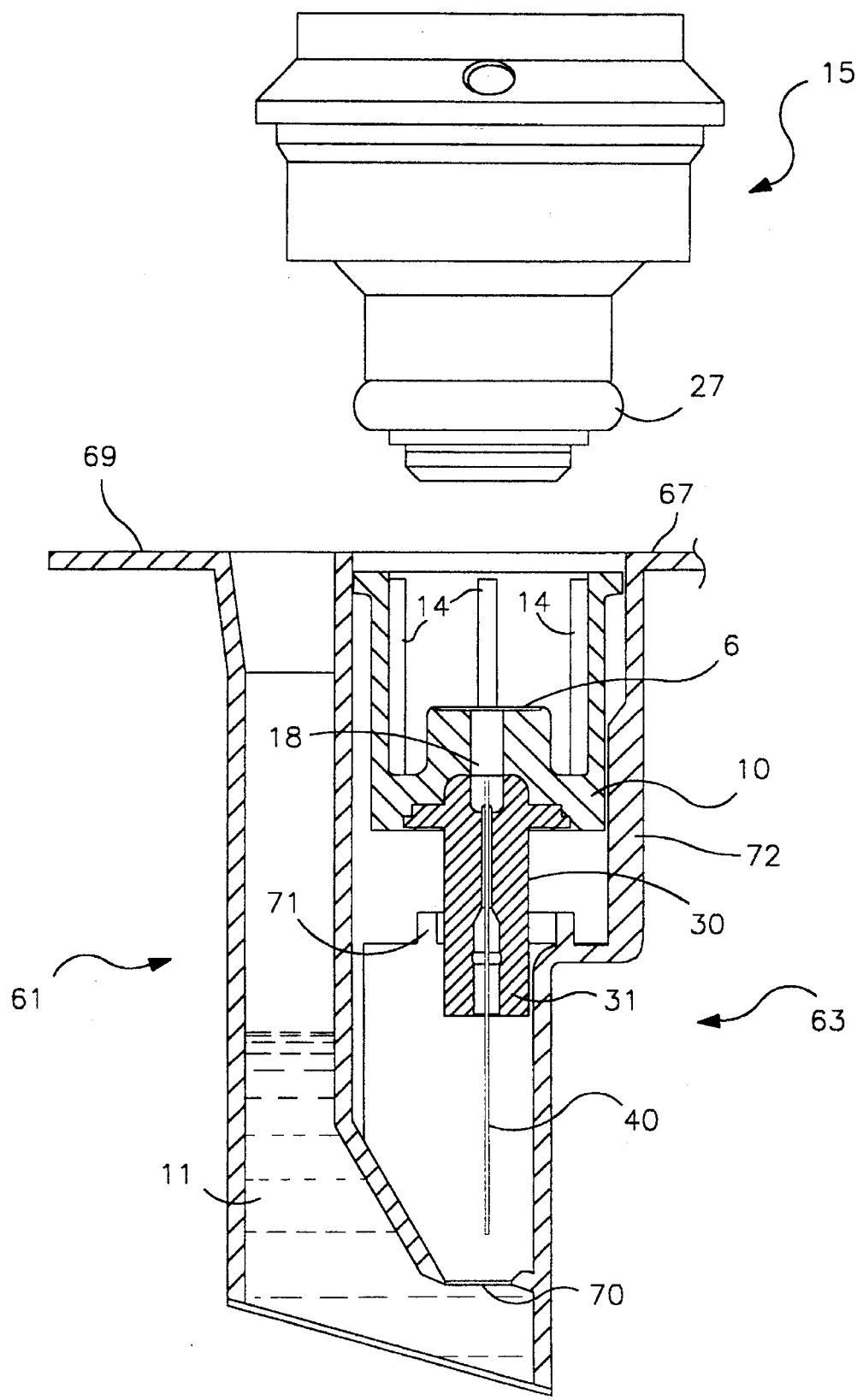
FIG. 2 is a cross section taken along line 2—2 of FIG. 1 wherein the device shown in FIG. 1 is in assembled form and further shows a portion of an instrument for use with the devices of the present invention.
Figure 3:
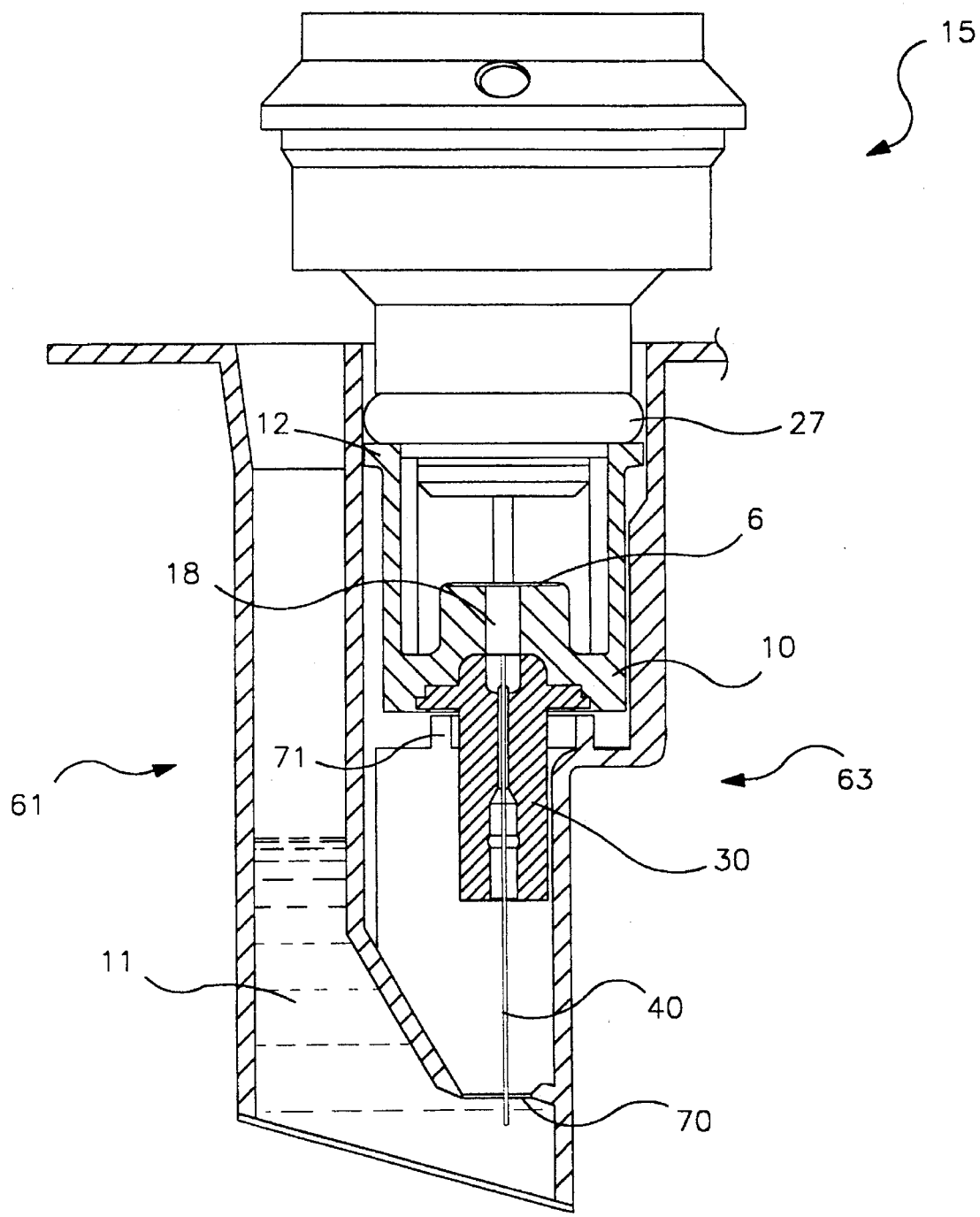
FIG. 3 is similar to FIG. 2, but shows the portion of the instrument having contacted and moved a component of the device shown in FIG. 2 from a first into a second position.
Figure 4:
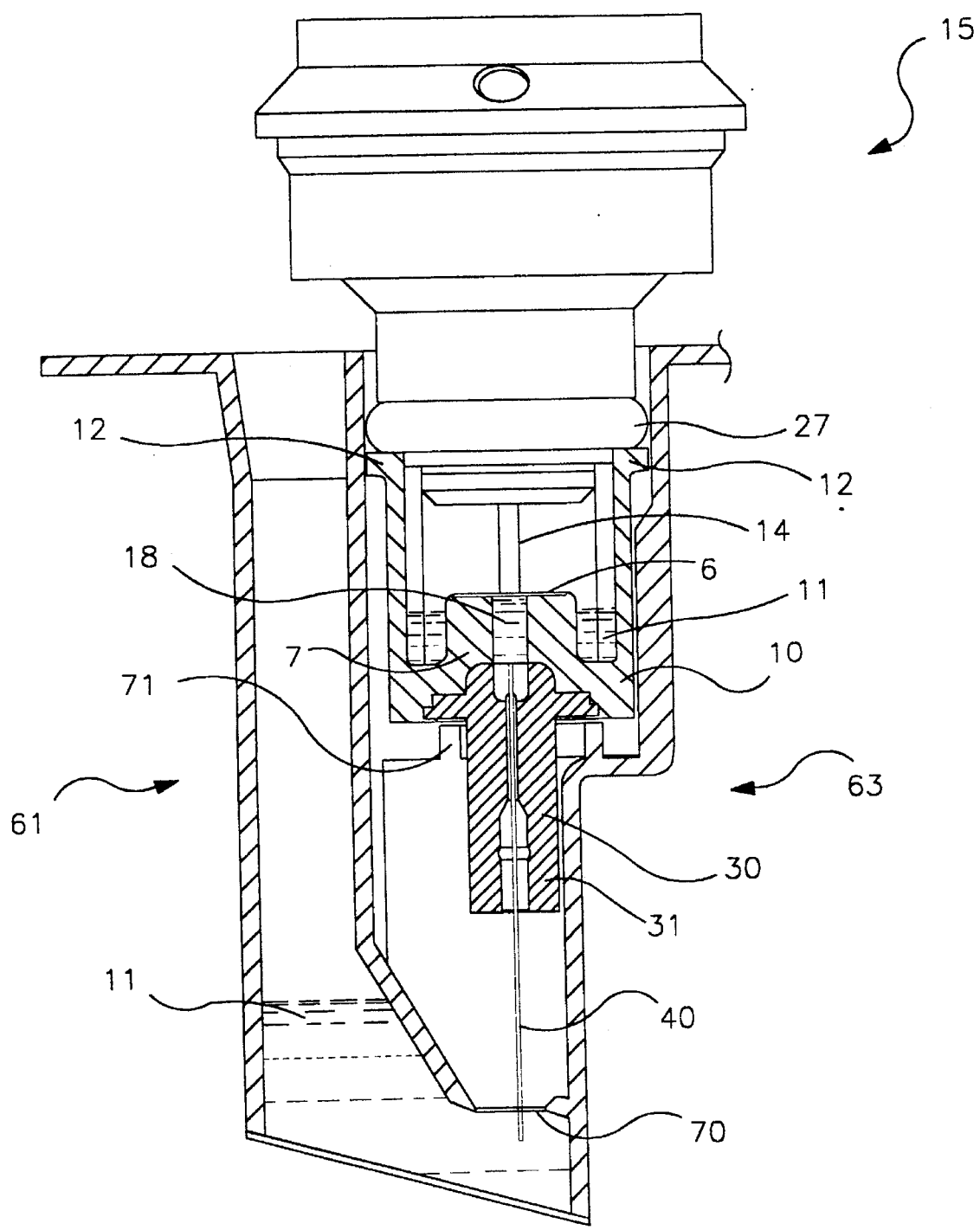
FIG. 4 is similar to FIG. 3 but shows sample having moved through the device.

FIG. 1 shows an isometric, exploded view of one preferred device in accordance with the present invention. A cross section of the device along line 2—2 of FIG. 1 in assembled form and containing sample 11 is shown in FIGS. 2, 3 and 4. FIGS. 2 to 4 also show a component of one instrument which can be used with the devices of the present invention. FIGS. 2 to 4 also illustrate different stages in one preferred assay of the present invention.

Referring now to FIG. 1, this device comprises a housing 60 which defines holding chamber 61 and test chamber 63. Housing 60 is provided with flange 67 and tab 69.

Housing 60 is provided with a removable top seal 62 which in the assembled device is hermetically sealed to flange 67 and closed at the bottom with bottom seal 66. In preferred embodiments, top seal 62 is pealable and completely removable from flange 67 so as not to leave any piece of seal which could interfere with creating a negative pressure within housing 60 as described hereinafter.

Top seal 62 is optionally provided with a desiccant not shown. Housing 60 serves as a storage package when top seal 62, desiccant and bottom seal 66 are in place. The desiccant material maintains chambers 61, 63 at a low humidity by absorbing any moisture that may permeate through housing 60 during storage.

Top seal 62 comprises a material which resists moisture, such as LCFlex 7075 Polyester/Polyethylene Coated Aluminum, a trademark of Jefferson Smurfit Corporation, Schaumburg, Ill. Bottom seal 66 comprises a material which efficiently transfers heat, such as a metallic foil, from the instrument to bring a blood sample to 37° C. before starting the test (body temperature).

The geometry of housing 60 which defines holding chamber 61 and test chamber 63 is selected to minimize the possibility of an air bubble being trapped in the device and in preferred embodiments the bottom of holding chamber 61 is sloped to minimize air entrapment when blood is added through opening 65. The section of housing 60 defining holding chamber 61 is tapered at opening 65 for ease of inserting, e.g., a pipette tip for delivering blood to holding chamber 61.

The geometry of the housing is selected to maximize surface contact of the blood to the heated surface of the housing, while at the same time minimizing the area of blood exposed to the air to minimize risk of sample degradation. In the embodiment shown in the figures, the L-shaped configuration of housing 60 accomplishes both of these objectives.

In the embodiment shown in the figures, housing 60 is provided with flange 67. The flange is designed to provide a large enough surface to affix removable top seal 62.

Flange 67 is also provided with tab 69 in which is punched type sense code 68. Under the action of the automated test instrument, the housing 60 is moved at a relatively steady speed beneath a reflective infrared sensor which is part of the instrument. The alternating punched holes and solid areas forming type sense code 68 in tab 69 of flange 67 are so situated that the infrared beam is alternatively reflected and not refected towards a detecting sensor. The resulting alternating high and low output of the detector can be interpreted as a series of binary digits which serve to uniquely identify the type of assay to be conducted. This general scheme is similar to that used in familiar bar code readers.

Sense code 68 also tells the instrument that a sample is inserted. In other words, it is both a presence detector and a type of test detector.

Figure 7:
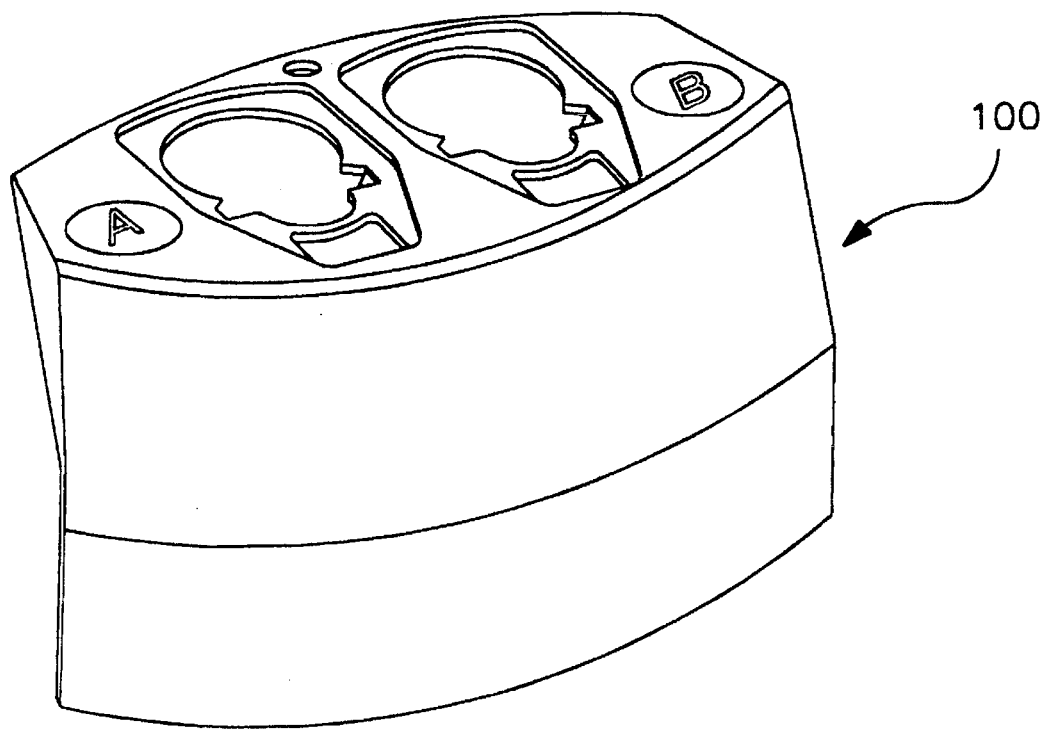
FIG. 7 shows a front isometric view of one cassette of the present invention.
Figure 8:
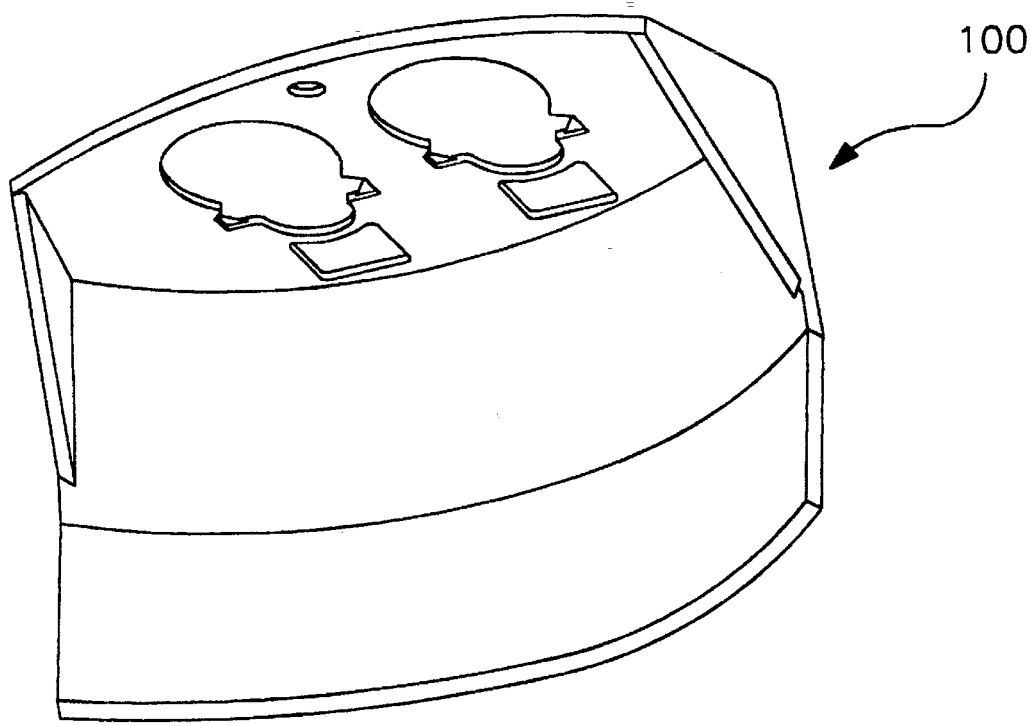
FIG. 8 shows a rear isometric view of the cassette shown in FIG. 7.

Flange 67 is also provided with cassette snaps 80 so that the housing 60 can be snapped into a cassette shown in FIGS. 7 and 8 which holds one or more of the present test cartridges in the right orientation to conveniently pipette sample in through opening 65 and minimize air entrapment.

In the embodiment shown, flange 67 has two parallel sides so that it is bowl feedable in an automated production line.

Test chamber 63 is adapted to receive sample cup 10. Sample cup 10 supports a reagent treated partition member 6 having aperture 9 therein and a capillary hub 30 which provides a mechanism to operably attach transfer member 40 to sample cup 10. The interior of sample cup 10 is provided with four vacuum chuck stop ribs 14 for positioning, two of which are shown in FIG. 1.

Housing 60 is adapted to mate with an instrument which can create a negative pressure in test chamber 63 or in a part of test chamber 63. In the embodiment shown, this is accomplished by rim 12 of sample cup 10 which comprises a part of test chamber 63. The instrument has a mating component which is capable of sealably mating with rim 12 of sample cup 10. In the embodiment shown in FIGS. 2 to 4, the mating component comprises vacuum chuck 15 shown. Vacuum chuck 15 is provided with 0-ring 27 which during the assay sealably meets rim 12. The contact is sufficient to enable vacuum chuck 15 to create a negative pressure in sample cup 10. Vacuum chuck 15 is moved by the instrument to contact rim 12 and to exert a downward pressure on sample cup 10 to move transfer member 40 towards pierceable member 70, causing it to pierce the pierceable member and extend into sample 11 in the holding chamber. Vacuum chuck stop ribs 14 in sample cup 10 limit the downward movement of vacuum chuck 15.

FIG. 2 shows a cross section view of the device shown in FIG. 1 along line 2—2 before vacuum chuck 15 has exerted downward pressure on sample cup 10. FIG. 3 shows a cross section view of the device shown in FIG. 2 after vacuum chuck 15 has moved to contact and move sample cup 10 downward so that the bottom of sample cup 10 is in contact with support member 71 and a transfer member, in this embodiment 40 has pierced pierceable member 70 and penetrated into sample 11. As shown in FIG. 3, support member 71 contacts the bottom of sample cup 10 under the downward pressure of the instrument.

The instrument is then able to create a negative pressure in test chamber 63, e.g., by pulling a vacuum. This vacuum or negative pressure causes sample 11 to flow from holding chamber 61 through capillary transfer member 40 into receiving chamber 18 and through aperture 11 in partition member 6 as shown in FIG. 4. In the case of test cartridges for use in the platelet function assay, reagents on partition member 6 activate the formation of a platelet plug which eventually occludes aperture 9 and the flow of sample through transfer member 40 ceases. The time required for the blood flow to cease is then compared with the time required for blood flow to cease when the platelet function of the blood is normal. A normal range within which blood flow should stop is obtained by testing normal blood.

Figures 5, 6:
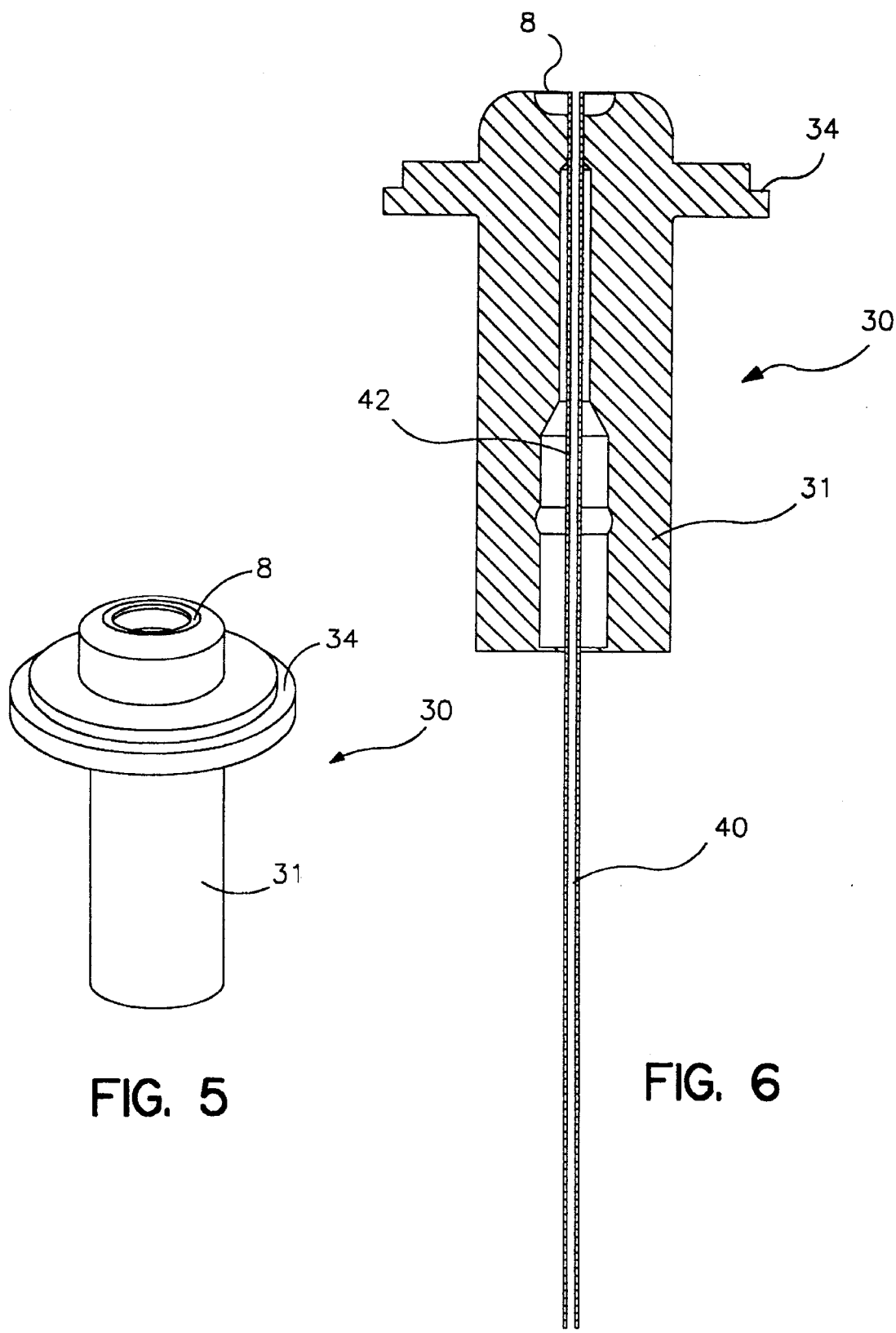
FIG. 5 is an enlarged isometric view of capillary hub 30 shown in FIG. 1.
FIG. 6 is an enlarged cross section view of capillary hub 30 with capillary 31 as shown in FIG. 2.

Capillary hub 30 is shown in detail in FIG. 5. FIG. 6 shows a cross section of a device wherein capillary 40 is glued to capillary hub 30 by means of glue placed in glue gap 42. Capillary hub 30 is affixed to sample cup 10 at weld surface 34 by ultrasonic welding.

In the embodiment shown, capillary hub 30 is molded as a separate piece to facilitate coating and punching an aperture in partition members which are fragile. However, sample cup 10 could be molded as a single piece which includes capillary hub 30 and capillary 40.

Before capillary hub 30 is assembled to sample cup 10, partition member 6 is welded to membrane seat 8 and one or more reagents are applied to the surface of partition member 6 which will face receiving chamber 18. Partition member 6 is then dried, and opening 9 shown in FIG. 1 is made in the dried membrane.

Opening 9 in partition member 6 is dimensioned so that under the conditions of the particular assay a plug will be formed and the opening closed. If the aperture is too small non-assay related blockages will occur. If it is too big then a plug will not form properly. For the platelet function test, the aperture is preferably between about 100 microns to about 200 microns, more preferably about 140 microns to 160 microns, most preferably about 150 microns. The dimension of the aperture in partition member 6 does not have a great influence on the initial flow characteristics in the device.

Receiving chamber 18 shown in FIGS. 2 and 3 is positioned in test chamber 63 between partition member 6 and capillary hub 30. Receiving chamber 18 is dimensioned so that blood entering from capillary 40 does not enter too close to the membrane and disturb the forming plug.

Partition member 6 is a porous or non-porous support matrix for the collagen and/or other agents which promote the clotting of blood. The preferred material has absorbency to liquids so that reagents can be applied yet has a stable structure so that a precise opening can be, for example, punched. In the platelet function test, adenosine 5' diphosphate (ADP) and collagen are preferred reagents for partition member 6.

Preferred porous partition members for use in the test cartridge and methods of the present invention include cellulose esters, ceramic, nylon, polypropylene, polyvinylidene fluoride (PVDF), and fiberglass. A particularly preferred porous partition member is a mixed cellulose ester (acetate and nitrate) membrane from Millipore.

In embodiments, wherein the partition member is provided with a collagen coating, a uniform layer of collagen around the aperture is highly desirable. The amount of collagen on the membrane is not particularly critical. A range of about 1–2 μg has been found to perform well in the platelet function assay. In one test cartridge of the present invention, collagen is provided to partition member and then the porous member is dried for storage in the housing under a hermetic seal.

ADP is known to be unstable in aqueous solutions, having a useful life of only about 4 hours. Accordingly, it is applied to the porous member just before use at a concentration of from about 1 mg/ml to about 90 mg/ml, more preferably about 45 mg/ml to about 55 mg/ml.

However, in one preferred test cartridge of the present invention, ADP is incorporated in a porous partition member, the partition member is dried and welded to sample cup 10, and stored under hermetically sealed conditions until ready for use. The ADP is brought into solution before use by applying a wetting solution.

In assay systems for testing platelet function, platelet aggregation modulation agents, such as ADP, are incorporated into the porous partition members of the present invention. The present invention also provides porous partition members having incorporated therein other standard modulating agents, such as ristocetin, arachidonic acid and salts thereof, thrombin, epinephrine, platelet activating factor (PAF), thrombin receptor agonist peptide (TRAP), and so forth which are useful in the evaluation of various aspects of platelet function.

The porous partition members for us in the test cartridges and methods of the present invention are also useful in whole blood and blood plasma coagulation assays to evaluate coagulation functions, similar to PT and PTT tests. In such embodiments, clot formation is initiated by blood contact with appropriate activators of extrinsic or intrinsic pathways which have incorporated in the porous partition member which ultimately causes cessation of blood flow through the porous partition member. The time required for cessation of blood flow to occur can be correlated, e.g., to the prothrombin time or the partial thromboplastin time for the patient. In contrast, present whole blood coagulation instruments rely on changes in optical signals or electrical signals upon formation of a clot.

Activators of the extrinsic pathway of prothrombin conversion suitable for incorporation in the porous partition members of the present invention include thromboplastin reagents, e.g., THROMBOPLASTIN-C®, Baxter-Dade. Activators of the intrinsic pathway suitable for incorporation in the porous partition members of the present invention include inosithin, and calcium chloride and/or activated cephaloplastin reagent (ACTIN®, Baxter-Dade). ACTIN® may be incorporated in the porous partition member or premixed with a whole blood sample to be tested. These tests can be carried out both on anticoagulated whole blood and on plasma samples.

The concentration of agent or agents in the porous partition member are selected so as to result in an aperture closure time which shows a difference between normal and abnormal coagulation parameters.

In the platelet function test, adenosine 5' diphosphate (ADP) is a preferred reagent for incorporation in the porous partition members of the invention. ADP is unstable in aqueous solution having a useful life of only about 4 hours. It was unexpectedly found that by incorporating ADP in a porous partition member, drying it and storing it at about 4° C. under hermetically sealed conditions, it is stable for about one and one-half years. By eliminating the need for a user to prepare ADP solutions for use in the assay, such porous partition members eliminate user error, permeation variability, and provide reproducible stimulation for platelet aggregation.

The aperture closure time with a normal blood sample depends in part upon the concentration of the biologically active substance incorporated in the membrane. The concentration of agents is selected so as to provide a convenient distinction between normal and abnormal coagulation parameter. This can be readily determined by one of ordinary skill in the art. The concentration ranges of similar reagents reported for use in aggregometry provide one starting point in determining the appropriate concentration range. Reagent concentrations are optimized keeping in mind the desired sensitivity of the assay. For example, it is desirable that the concentration of ADP be sufficient to detect mild platelet dysfunction, but not so low as to introduce variable results.

A threshold amount is needed for complete activation and aggregation and if mild platelet disfunction is being studied, then a smaller amount of reagent is used. It can be seen that a balance between the sensitivity of the test and obtaining reproducible results is desired.

As shown in FIGS. 2 and 3, test chamber 63 is provided with a two position support for sample cup 10, the support comprising support member 71 and crush rib 72. Support member 71 has a central opening dimensioned to permit section 31 of capillary hub 30 to pass therethrough. As shown in FIG. 2, crush rib 72 (others not shown) maintain sample cup 10 in a first position so that capillary 40 is above but not in contact with pierceable membrane 70. As shown in FIG. 3, sample cup 10 has been moved into a second position whereby crush ribs 72 have been compressed, sample cup 10 is in contact with and held in position by support member 71, section 31 of capillary hub 30 has passed through support member 71, and capillary 40 has been moved towards and through piercable membrane 70 to project into holding chamber 61 and into sample 11 disposed therein.

Sample is caused to flow from holding chamber 61 to test chamber 63 by the negative pressure created by the instrument.

The initial rate of flow through the device is controlled by varying the length and the inner diameter of the capillary. In platelet function tests, for a sample volume of about 500 to 800 µl it is preferred that the initial flow rate of blood through the device be from about 100 µl to about 200 µl per minute. It is believed that diameters much less than 100 micron will have an effect on platelets. Accordingly, the preferred inner diameter of capillary 40 is from about 100 to 220 microns. A particularly preferred inner diameter is about 150–210 µ and a preferred length of the capillary is about 0.6–1.2 inches long. In an especially preferred embodiment the inner diameter of the capillary is about 200±10 microns and the length of the capillary is about 1.2 inches. With this configuration and flow, the aperture in the membrane will close in about 1 to 3 minutes if the blood is normal.

If it is desired to make the capillary shorter for some assays, the inner diameter of the capillary can be decreased to maintain the same flow rate through the system or the sample volume could be adjusted accordingly.

The capillary can be made of any material that can hold a tight tolerance with respect to the inner diameter, has a relatively smooth inner surface and is compatible with blood, i.e., not an activator of blood. In embodiments wherein sample cup 10 is molded as a single piece including capillary hub 30, a convenient material for the capillary hub 30 is plastic. A convenient material for the capillary is stainless steel.

The components of the present invention are manufactured from materials that are compatible with blood. In the platelet function test, the materials are selected so that they do not activate platelets. Polypropylene is a preferred material for the housing. However, other plastics such as polyethylene terephthalate (PET) are also acceptable. Polypropylene is a preferable plastic when welding will be used to assemble parts of the device.

An operator prepares the disposable device shown in the figures for use by removing the top foil 62 and attached desiccant material, if present. In one preferred embodiment the device is snapped into cassette 100 shown in FIGS. 7 and 8. The operator then transfers the sample to be tested into holding chamber 61 through opening 65 by use of a pipette or similar device. Cassette 100 containing the disposable device with the loaded sample is placed into an automated instrument where the sample is heated to the required test temperature.

The instrument is able to determine the heating time and other test parameters by reading type sense code 68 located on tab 69 of flange 67. Heating of sample 11 is augmented by the higher heat transfer characteristic of bottom seal 66, the outer surface of which is in close proximity to a heater block in the instrument and the inner surface is in contact with sample 11.

The sample in holding chamber 61 is isolated from test chamber 63 during the incubation period by pierceable member 70 which is shown in FIG. 2. Referring now to FIGS. 2 and 3, at the end of the incubation period, the automated instrument initiates the testing cycle by moving sample cup 10/capillary hub 30 assembly from position A shown in FIG. 2 to position B shown in FIG. 3, which causes transfer member 40 to pass through pierceable member 70 into holding chamber 61 and thus into contact with sample 11. The instrument exerts a downward pressure on sample cup 10 through vacuum chuck 15 which sealably mates with rim 12 of sample cup 10, thereby creating a seal between the mating portion of the instrument and rim 12. The instrument then creates a negative pressure within sample cup 10 which causes sample to be drawn up through capillary 40 to receiving chamber 18 and through the opening in partition member 6.

The disposable device, together with the sample, is removed from the instrument and discarded at the completion of the test. The cassette is reused.

In one preferred test cartridge of the present invention, lyophilized ADP or epinephrine bitartrate was incorporated in a porous partition member comprising a membrane. These agents were dissolved in a sodium acetate-acetic acid buffer (pH 3.5) containing 5% glucose (osmolality 280 mOsm/kg). The concentration of ADP solution used for incorporation into the membrane was 50 mg/ml, and that of the epinephrine solution was 10 mg/ml.

A strip of membrane was spot-coated with 1 µL of ADP or epinephrine solution. Therefore, each membrane placed in a test cartridge contained 50 µg of ADP or 10µg of epinephrine. The membrane was then spot-coated with 1 µL of fibrillar Type I collagen suspension from horse tendon available from Nycomed AG.

Spot-coating involved putting spots of liquid agent on a strip of membrane. After spot-coating, the membrane was placed in a forced air drying chamber for 25 minutes for drying of the ADP or epinephrine, and formation of a collagen film on the coated areas. Once dried, an aperture is, e.g., was punched in the center of the spot and a membrane disk was cut from the membrane strip. The membrane disk was inserted in a test cartridge.

Prior to the blood test, saline was dispensed onto the membrane to bring the ADP or epinephrine into solution. However, it has been found that the test progressed normally, even without saline dispensed onto the membrane. The blood sample alone can dissolve the dried ADP or epinephrine present in the membrane.

For both tests, blood was aspirated through the aperture at a constant pressure gradient of about 40 mbar, and the time required for cessation of blood flow to occur was determined.

Various configurations of the major components could be implemented to achieve similar results such as combining the sample cup, capillary hub and capillary into one part or locating the sample storage area entirely beneath the sample cup/capillary hub assembly.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

What is claimed is:

1. A test cartridge for use in blood coagulation, enzyme immunoassays, cell ligand, cell—cell interactions, and platelet aggregation assays of a liquid sample, the test cartridge comprising a housing through which the liquid sample flows during the assay, the housing defining:
   (a) a test chamber and a holding chamber for holding a liquid sample, wherein the holding chamber and test chamber are separated by a pierceable member;
   (b) a partition member disposed in the test chamber, the member having an opening therethrough and comprising at least one reagent for the assay; and
   (c) a transfer member movably mounted in the test chamber so that it can be moved towards and pierce the pierceable member and contact the liquid sample in the holding chamber;

whereby when the transfer member has moved towards and pierces the pierceable member to contact the liquid sample and a negative pressure is created in the test chamber, liquid sample moves through the transfer member, into the test chamber and through the opening in the partition member.

2. A test cartridge in accordance with claim 1, further comprising a sample cup movably supported within the test chamber and a vacuum means sealably mating with said sample cup, whereby when said sample cup and said vacuum means exerts a downward pressure on the transfer member, said transfer member moves towards and pierces the pierceable member.

3. A test cartridge in accordance with claim 1, further comprising the partition member disposed in the sample cup.

4. A test cartridge in accordance with claim 1, wherein at least one reagent is collagen, an antigen, an antibody or a ligand for binding cells.

5. A test cartridge in accordance with claim 1, wherein the partition member comprises a porous material.

6. A test cartridge in accordance with claim 5, wherein the porous partition member comprises a porous material having an aperture and having incorporated therein at least one agent which initiates a blood coagulation process or platelet aggregation in blood.

7. A test cartridge according to claim 6, wherein the agent which initiates the blood coagulation process comprises at least one activator of the extrinsic or intrinsic pathways of prothrombin conversion.

8. A test cartridge according to claim 7, wherein the activator of the extrinsic or intrinsic pathways of prothrombin conversion comprises a thromboplastin reagent or an activated cephaloplastin reagent.

9. A test cartridge according to claim 7, wherein the thromboplastin reagent comprises THROMBOPLASTIN-C® and the activated cephaloplastin reagent comprises ACTIN®.

10. A test cartridge according to claim 6, wherein the agent which initiates platelet aggregation in blood comprises ADP, ristocetin, arachidonic acid, thrombin, epinephrine, platelet activator factor (PAF), or thrombin receptor agonist peptide (TRAP).

11. A test cartridge according to claim 10, further comprising collagen.

12. A test cartridge according to claim 6, wherein the porous partition member comprises a membrane, ceramic, nylon, polypropylene, polyvinylidene fluoride or fiberglass.

13. A test cartridge according to claim 6, wherein the membrane comprises a mixed cellulose ester membrane.

14. A test cartridge according to claim 1, wherein the holding chamber is L-shaped, the bottom of the L forming the bottom of the holding chamber and being angled downwardly.

15. A test cartridge according to claim 14, wherein the bottom of the holding chamber comprises a material which is capable of enhancing heat transfer.

16. A test cartridge according to claim 1, wherein the top of the housing is provided with a removable seal which seals both holding and test chambers.

17. A test cartridge according to claim 16, wherein the side of the removable disposed towards the inside of the housing is provided with a desiccant.

18. A test cartridge according to claim 1, wherein the top of the housing is provided with a flange having a type sense code.

19. A test cartridge for use in an assay system for testing a coagulation function of blood, the test cartridge comprising a housing through which the blood flows, wherein the housing defines:
   (a) a test chamber and a holding chamber for holding a sample of the blood to be tested wherein the holding chamber and test chamber are separated by a pierceable member;
   (b) a partition member disposed in the test chamber, the partition member having an opening therethrough and containing at least one reagent which activates at least one pathway of the coagulation of blood;
   (c) a transfer member movably mounted in the test chamber so that it can be moved towards and pierce the pierceable member; and
   (d) a receiving chamber disposed in the test chamber between the partition member and the transfer member for receiving blood from the transfer member;

whereby when blood is disposed in the holding chamber and the transfer member has been moved towards and pierces the pierceable member to contact the blood and a negative pressure is created in the test chamber, blood moves through the transfer member into the receiving chamber and through the opening in the partition member.

20. A test cartridge according to claim 19, wherein the reagent comprises at least one activator of the extrinsic or intrinsic pathways of prothrombin conversion.

21. A test cartridge according to claim 20, wherein the activator of the extrinsic or intrinsic pathways of prothrombin conversion comprises a thromboplastin reagent or activated cephaloplastin reagent.

22. A test cartridge according to claim 21, wherein the thromboplastin reagent comprises THROMBOPLASTIN-C® and the activated cephaloplastin reagent comprises ACTIN®.

23. A method of testing platelet function which comprises passing blood through a test cartridge, the test cartridge comprising a housing through which the blood flows during the assay, wherein the housing defines:
   (a) a test chamber and a holding chamber for holding a sample of the blood to be tested wherein the holding chamber and test chamber are separated by a pierceable member;
   (b) a partition member disposed in the test chamber, the partition member having an opening therethrough and containing at least one reagent which activates the aggregation of platelets;
   (c) a transfer member movably mounted in the test chamber, wherein said transfer member can be moved towards and pierce the pierceable member; and
   (d) a receiving chamber disposed in the test chamber between the partition member and the transfer member for receiving blood from the transfer member;

wherein the method comprises the steps of:

(i) providing a sample of blood to the holding chamber;

(ii) preincubating the sample under predetermined conditions;

(iii) moving the transfer member towards and through the pierceable member and into contact with the blood in the holding chamber;

(iv) causing the pressure in the test chamber to become sufficiently negative to cause blood to flow through the transfer member into the receiving chamber and through the opening in the partition member;

(v) measuring the amount of time it takes for the formation of a platelet plug at the opening in the partition member thereby stopping the flow of blood; and (vi) correlating the time determined in step (v) with a predetermined value.

24. A test cartridge according to claim 13, wherein the mixed cellulose ester membrane comprises acetate and nitrate.

* * * * *